(12) United States Patent
Xi et al.

(10) Patent No.: US 12,714,833 B2
(45) Date of Patent: Aug. 25, 2026

(54) BALLOON CATHETER AND ABLATION SYSTEM

(71) Applicant: SHANGHAI MICROPORT EP MEDTECH CO., LTD., Shanghai (CN)

(72) Inventors: Yunzhu Xi, Shanghai (CN); Bo Liang, Shanghai (CN); Qiming Wu, Shanghai (CN); Sunwu Yao, Shanghai (CN); Li Huang, Shanghai (CN); Yiyong Sun, Shanghai (CN)

(73) Assignee: SHANGHAI MICROPORT EP MEDTECH CO., LTD., Shanghai (CN)

( * ) Notice: Subject to any disclaimer, the term of this patent is extended or adjusted under 35 U.S.C. 154(b) by 509 days.

(21) Appl. No.: 18/269,410

(22) PCT Filed: Sep. 28, 2021

(86) PCT No.: PCT/CN2021/121399
§ 371 (c)(1),
(2) Date: Jun. 23, 2023

(87) PCT Pub. No.: WO2022/134714
PCT Pub. Date: Jun. 30, 2022

(65) Prior Publication Data

US 2024/0050711 A1 Feb. 15, 2024

(30) Foreign Application Priority Data

Dec. 25, 2020 (CN) ........................ 202011562243.6

(51) Int. Cl.
*A61B 5/01* (2006.01)
*A61M 25/10* (2013.01)
*A61B 18/00* (2006.01)

(52) U.S. Cl.
CPC ............... *A61M 25/10* (2013.01); *A61B 5/01* (2013.01); *A61B 2018/0022* (2013.01); *A61B 2018/00351* (2013.01)

(58) Field of Classification Search
CPC .......... A61M 25/10; A61B 5/01; A61B 5/015; A61B 5/6853; A61B 2018/0022;
(Continued)

(56) References Cited

U.S. PATENT DOCUMENTS 5,335,669 A 8/1994 Tihon et al.
2003/0060820 A1 3/2003 Maguire et al.
(Continued)

FOREIGN PATENT DOCUMENTS

CN 1674836 A 9/2005
CN 106512167 A 3/2017
(Continued)

*Primary Examiner* — Niketa Patel
*Assistant Examiner* — Joshua Brendon Solomon
(74) *Attorney, Agent, or Firm* — MUNCY, GEISSLER, OLDS & LOWE, P.C.

(57) ABSTRACT

The present invention relates to a balloon catheter and an ablation system. The balloon catheter includes a catheter body, a balloon, a temperature-sensing element and a restricting member. The balloon is disposed at a distal end of the catheter body. The temperature-sensing element includes a temperature-sensing module and a wire. The temperature-sensing module is disposed on the balloon or the catheter
(Continued)

body, and part of the wire of the temperature-sensing element is arranged in a cavity of the catheter body so as to extend in an axial direction of the cavity of the catheter body. The restricting member is disposed within the cavity of the catheter body and configured to positionally restrict the wire of the temperature-sensing element within the cavity of the catheter body. According to the present invention, the restricting member restricts and protects the wire of the temperature-sensing element, thereby avoiding the risk of the wire being stretched and possibly broken during expansion or contraction of the balloon or during movement of the catheter. Moreover, the wire is avoided from hindering movement of the catheter body.

14 Claims, 7 Drawing Sheets

(58) Field of Classification Search
CPC .......... A61B 2018/00351; A61B 2018/00375; A61B 2018/00404; A61B 2018/00434; A61B 2018/00511; A61B 2018/00577; A61B 2018/00797; A61B 2018/0212; A61B 2018/00023; A61B 2018/00714; A61B 2018/00964; A61B 2018/0262; A61B 18/02; A61B 18/00
See application file for complete search history.

(56) References Cited

U.S. PATENT DOCUMENTS

2004/0002749 A1* 1/2004 Joye ...................... A61B 18/02 607/113
2005/0203597 A1 9/2005 Yamazaki et al.
2009/0318798 A1* 12/2009 Singh .................... A61B 1/012 604/544
2012/0143130 A1* 6/2012 Subramaniam ....... A61M 25/10 604/99.01
2012/0296232 A1* 11/2012 Ng .................... A61B 18/1492 600/554
2015/0216580 A1* 8/2015 Mihalik ............ A61B 18/1492 606/21
2015/0374436 A1* 12/2015 Subramaniam .... A61B 18/1492 606/41
2017/0367760 A1 12/2017 Crozier et al.
2020/0085496 A1 3/2020 Sharma et al.

FOREIGN PATENT DOCUMENTS

CN 107427321 A 12/2017
CN 108175400 A 6/2018
CN 109843201 A 6/2019
WO WO-2010103502 A2 9/2010
WO WO-2020035919 A1 2/2020
WO WO2020036886 A1 2/2020
WO WO2020155978 A1 8/2020

* cited by examiner

BALLOON CATHETER AND ABLATION SYSTEM

TECHNICAL FIELD

The present invention relates to the field of medical instruments and, in particular, to a balloon catheter and an ablation system.

BACKGROUND

Patients with atrial fibrillation are at very high risk for stroke. Atrial fibrillation is a condition featuring rapid and irregular beating of the atrium and the loss of contractility of the heart, which make it easy for blood to stagnate in the atrium and form clots. When such clots break free and travel through the arteries to the brain, a stroke may occur. This can be treated by isolating the pulmonary vein potential through ablating a portion of the pulmonary vein using energy delivered from an interventional catheter. Hypertension is characterized by high prevalence, low awareness and significant harmfulness. Experimental data have suggested a correlation of hypertension to elevated renal sympathetic nerve activity (RSNA). Blocking the renal sympathetic nerves by ablation can not only lower blood pressure, but can also benefit organ-specific chronic diseases arising from sympathetic over-activity.

Ablation can be accomplished with a cryoballoon, which is designed based on anatomical considerations and adapted to be brought into contact with and freeze target tissue. Cryoballoon ablation is characterized by the ability to form a continuous ablation line within a single procedure. During such a procedure, a physician may insert a catheter, which is arranged with a balloon at its distal end and connected to a cryogenic freezing unit at its proximal end, through a percutaneous puncture into the cardiac muscle tissue so that the balloon is located around the pulmonary vein orifice. The balloon is then dilated to an extent allowing desired contact of an outer wall thereof with myocardial tissue, and a cryogenic liquid is injected from a liquid inlet of the catheter directly onto an inner surface of the balloon, where it is instantly vaporized at a higher temperature of the tissue and absorbs heat, freezing and ablating the tissue that is in contact with the balloon. In general terms, the formation of an effective ablation lesion in myocardial tissue requires maintaining a target low temperature for a sufficiently long time. To this end, a cryoablation balloon catheter is typically provided, in the middle of the balloon, with temperature sensing elements for monitoring an internal temperature inside the balloon, which is then used as a basis for estimating an outer surface temperature of the balloon. However, in practice, there is a possibility of a significant deviation of the estimate from the actual value, which may have a direct adverse impact on the ablation outcomes.

In the prior art, there has been disclosed a balloon catheter with linear-shaped sensors. The ability of these temperature-sensing elements to displace relative to a balloon imparts to them desirable compliance with expansion or contraction of the balloon. However, the applicant has found that, when more such temperature-sensing elements are incorporated in the balloon, more wires must be received between an outer tube and a core rod of the balloon catheter to establish electrical connections with the temperature-sensing elements. During ablation, as a result of expansion and contract of the balloon and rotation, twisting and other motions of the catheter, the wires will be forced to move accordingly. Once interference occurs between different wires during such movement, the wires will have limited mobility and tend to be broken due to otherwise possibly resulting forces. When this happens, the wire will no longer enable temperature monitoring of corresponding balloon surface portions, affecting use of the balloon catheter. Moreover, intertwining of wires will hinder movement of the core rod, affecting the surgical procedure and increasing surgical complexity.

SUMMARY OF THE INVENTION

In order to solve the above-described problems, it is an object of the present invention to provide a balloon catheter and an ablation system, in which restricting members disposed over wires of temperature-sensing elements can effectively prevent interference between the wires and thereby avoid their breakage due to otherwise possibly resulting forces. Moreover, the wires can be avoided from hindering movement of a catheter body. In this way, higher reliability of the instrument and lower surgical complexity can be achieved.

The above and other related objects are attained by a balloon catheter provided in the present invention, which comprises a catheter body, a balloon, a temperature-sensing element and a restricting member,

- the balloon disposed at a distal end of the catheter body, the temperature-sensing element comprising a wire and a temperature-sensing module, the temperature-sensing module disposed on the balloon or the catheter body, part of the wire of the temperature-sensing element arranged in a cavity of the catheter body so as to extend in an axial direction of the cavity of the catheter body,
- the restricting member disposed within the cavity of the catheter body and configured to positionally restrict the wire of the temperature-sensing element within the cavity of the catheter body.

Optionally, the catheter body may comprises an outer tube and a core rod disposed in the outer tube, the core rod protruding at a distal end thereof out of the outer tube, the outer tube and the core rod defining an annular cavity therebetween, wherein the balloon is connected at a distal end thereof to the core rod and at a proximal end thereof to the outer tube; the cavity of the catheter body comprises the annular cavity; and the restricting member is disposed in the annular cavity.

Optionally, a plurality of temperature-sensing elements may be included,

- wherein the restricting members may be as many as the number of temperature-sensing elements, wherein the restricting members are spaced apart from one another within the cavity of the catheter body, and the wires of the temperature-sensing elements are passed through the restricting members respectively, or a number of restricting members may be included, which number is at least one and smaller than the number of temperature-sensing elements, wherein some of the wires of the temperature-sensing elements pass through the restricting members, and each of the restricting member is configured for passage therethrough by the wire of one of the temperature-sensing elements.

Optionally, non-adjacent ones of the wires of the temperature-sensing elements are equipped with the restricting members, or at least adjacent ones of the restricting members may be staggered in the axial direction of the cavity of the catheter body.

Optionally, the restricting member may be fixedly connected to an inner wall surface of the outer tube or an outer inner wall surface of the core rod, or the balloon catheter may further comprise a control handle disposed at a proximal end of the catheter body, wherein the restricting member is fixedly connected to the control handle.

Optionally, a plurality of restricting members may be included, which are circumferentially spaced apart around an axis of the core rod and connected in series to form a ring-shaped structure.

Optionally, the restricting members may comprise sleeves configured for allowing the wire of the temperature-sensing element to pass through so as to positionally restrict the wire of the temperature-sensing element, wherein the sleeves are connected in series to form the ring-shaped structure.

Alternatively, the restricting members may comprise annular rings configured for allowing the wire of the temperature-sensing element to pass through so as to positionally restrict the wire of the temperature-sensing element, wherein the annular rings are connected in series to form the ring-shaped structure, and each adjacent two of the annular rings are connected by one linear-shaped elastomer.

Optionally, the restricting members may comprise a plurality of first restricting members and a plurality of second restricting members, the first restricting members configured to positionally restrict the wire of the temperature-sensing element, the second restricting members configured to positionally restrict the first restricting members.

Additionally, the first restricting members may be circumferentially spaced apart around the axis of the core rod.

Further, the number of the second restricting members may be smaller than that of the first restricting members, wherein some of the first restricting members are disposed thereover with the second restricting members, and the second restricting members are connected in series to form the ring-shaped structure. Alternatively, the number of the second restricting members may be equal to that of the first restricting members, wherein each of the first restricting members is disposed thereover with a respective one of the second restricting members, and the second restricting members are connected in series to form the ring-shaped structure.

Optionally, the first restricting members may be sleeves and the second restricting members may be annular rings, wherein the sleeves are disposed within the annular rings and configured for allowing the wire of the temperature-sensing element to pass through; the annular rings are connected in series to form the ring-shaped structure; and each adjacent two of the annular rings are connected by one linear-shaped elastomer.

Optionally, one ring-shaped structure or a plurality of ring-shaped structures spaced apart along the axial direction of the cavity of the catheter body may be included.

Optionally, a plurality of temperature-sensing elements may be included, wherein part of the wire of each of the temperature-sensing elements is arranged in the cavity of the catheter body so as to extend in the axial direction of the cavity of the catheter body; each of the restricting members that form the ring-shaped structure is inserted therein with the wire of one of the temperature-sensing elements; and the number of the restricting members that form the ring-shaped structure is smaller than or equal to the number of the temperature-sensing elements.

Optionally, the restricting member may comprise a sleeve configured for movable insertion and thus positional restriction therein of the wire of the temperature-sensing element, the sleeve comprising narrower portions and at least one broader portion, the narrower portions having a luminal cross-sectional area smaller than a luminal cross-sectional area of the broader portion, wherein the wire of the temperature-sensing element comprises extensions and at least one curved portion, the curved portion configured to be able to be elongated or compressed, the extensions disposed in the narrower portions, the curved portion disposed in the broader portion.

Optionally, a plurality of temperature-sensing elements may be included, part of the wire of each of the temperature-sensing elements arranged in the cavity of the catheter body so as to extend in the axial direction of the cavity of the catheter body, wherein as many sleeves as the number of temperature-sensing elements may be included, wherein the sleeves are spaced apart within the cavity of the catheter body; the wires of the temperature-sensing elements movably pass through the sleeves respectively; and the broader portions of the sleeves over the wires of at least adjacent ones of the temperature-sensing elements are staggered in the axial direction of the cavity of the catheter body, or a number of sleeves may be included, which number is at least one and smaller than the number of temperature-sensing elements, wherein some of the wires of the temperature-sensing elements movably pass through the sleeves; each of the sleeves is configured for passage therethrough of the wire of one of the temperature-sensing elements; and the wires of the temperature-sensing elements that are equipped with the sleeves are non-adjacent ones, or the broader portions of the sleeves over the wires of at least adjacent ones of the temperature-sensing elements are staggered in the axial direction of the cavity of the catheter body.

Optionally, the balloon may be a double-layered balloon, wherein a plurality of temperature-sensing elements are included, with their temperature-sensing modules being arranged in an interlayer space of the double-layered balloon and/or on a portion of the catheter body located within the double-layered balloon.

The above and other related objects are also attained by an ablation system provided in the present invention, which comprises the balloon catheter as defined above, an ablation energy output device and a control device, the ablation energy output device in communication with the balloon catheter, the ablation energy output device configured to provide ablation medium to the balloon catheter, the control device configured to control, based on temperature information detected by the temperature-sensing element(s), the ablation energy output device to adjust a temperature of the ablation medium so as to maintain a surface temperature of the balloon within a predefined ablation temperature range.

Compared with the prior art, the balloon catheter and the ablation system of the present invention have the following advantages:

First, the restricting member can positionally restrict and protect the wire of the temperature-sensing element, increasing its mobility when stress during expansion or contraction of the balloon or during movement of the catheter. As a result, the risks of breakage of the wire due to otherwise possibly resulting forces or tangling there are reduced, thereby ensuring reliable temperature monitoring of the balloon catheter. Moreover, the wire is avoided from hindering movement of the catheter body, reducing surgical complexity.

Second, through accommodating the curved portion (e.g., a serpentine portion) of the wire in the broader portion of the restricting member, sufficient mobility of the curved portion when stressed during expansion or contraction of the balloon or during movement of the catheter is ensured, thereby additionally ensuring that the wire will not be stressed and broken and increasing the reliability of temperature monitoring.

Third, in case of a plurality of temperature-sensing elements, a plurality of restricting members may be included for positional restriction of their wires. For example, only non-adjacent ones, or all, of the wires may be restricted by using the restricting members. This can effectively avoid interference between the multiple wires, satisfactorily overcoming the problems of wire breakage and hindered catheter movement from a great number of wires. In particular, when the restricting members are connected in series into a ring-shaped structure, or when second restricting members are disposed over the first restricting members and connected in series into a ring-shaped structure, positional restriction of the first restricting members can be additionally provided, which can avoid interference between the first restricting members within the cavity of the catheter body. As a result, the sleeves will less hinder movement of the catheter body, resulting in an additional reduction in surgical complexity.

BRIEF DESCRIPTION OF THE DRAWINGS

In order to more clearly explain embodiments of the present invention or the prior art, the accompanying drawings, to which reference is to be made in connection with the following description of the embodiments, will be briefed below. Apparently, these drawings show only some embodiments of the present invention, and those of ordinary skill in the art can obtain other drawings in light of those contained herein, without paying any creative effort.

Figure 1:
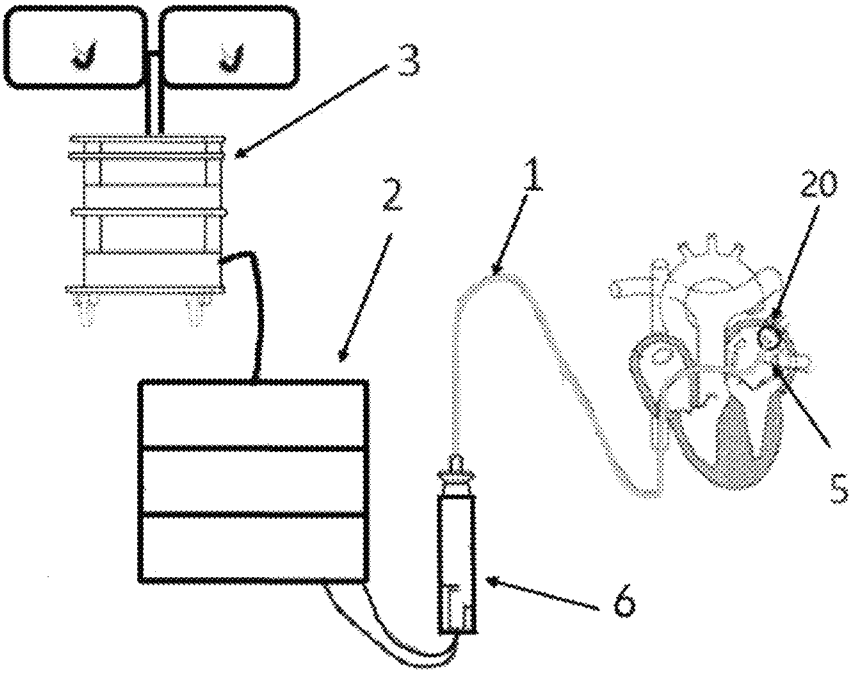
FIG. 1 schematically illustrates cardiac ablation performed with an ablation system according to a preferred embodiment of the present invention.

In these figures,

1 denotes an ablation catheter; 2, an ablation energy output device; 3, a control device; 4, the ostium of a renal artery; 5, the pulmonary vein; 6, a control handle; 7, a renal artery; 8, a temperature measurement point; 9, an electrical input/output interface; 10, a lumen access interface; 11, a fluid interface; 13, a catheter body; 131, an outer tube; 132, a core rod; 15, a second temperature-sensing element; 16, an area to be ablated; 17, a first temperature-sensing element; 18, a radiopaque marker; 19, a soft tip; 20, a double-layered balloon; 21, an outer balloon layer; 22, an inner balloon layer; 23, a securing member; 24, a wire; 241, a curved portion; 242, an extension; 25, a sleeve; 251, a broader portion; 252, a narrower portion; 27, a fluid inlet tube; 28, a traction thread tube; 29, an annular ring; 30, a dotted box; 31, a ring-shaped structure; and 32, a linear-shaped elastomer.

DETAILED DESCRIPTION

The present invention will become more apparent and can be readily understood from the following detailed description of a few specific embodiments thereof made in conjunction with the accompanying drawings. Of course, the present invention is not limited to these specific embodiments and general alternatives well known to those skilled in the art are also contemplated. While the present invention will be described in greater detail with reference to the annexed schematic drawings, these figures are presented only for the purpose of facilitating the detailing of the disclosed embodiments rather than limiting the present invention in any sense.

In the following, each of the embodiments is described as having one or more technical features. However, this does not mean that the present invention must be practiced necessarily with all such technical features, or separately with some or all the technical features in any of the embodiments. In other words, as long as the present invention can be put into practice, a person skilled in the art may choose some or all of the technical features in any of the embodiments or combine some or all of the technical features in different embodiments based on the teachings herein and depending on relevant design specifications or the requirements of practical applications. In this way, the present invention can be carried out more flexibly.

As used herein, the terms “proximal” and “distal” are intended to refer to relative orientations, relative positions and directions between components of a medical device or actions thereof, as viewed by a physician operating the device. Without wishing to be limiting, a “proximal end” usually refers to an end closer to the operator, and a “distal end” to an end first enters the body of a patient, during normal operation of the medical device. As used herein, the singular forms “a”, “an” and “the” include plural referents, unless the context clearly dictates otherwise. As used herein, the term “or” is generally employed in the sense including “and/or” unless the context clearly dictates otherwise. Further, the term “circumferential” generally refers to a direction about an axis of a balloon catheter, and the term “axial” generally refers to a direction parallel to the axis of the balloon catheter.

As discussed in the Background section, Patent Publication No. CN109646106 B discloses a balloon catheter with linear-shaped sensors disposed in an interlayer space of a double-layered balloon thereof. The ability of these temperature-sensing elements to displace relative to the balloon imparts to them desirable compliance with expansion or contraction of the balloon. However, the applicant has found that, when more such temperature-sensing elements are deployed in the interlayer space, more wires must be received in a cavity of a catheter body, which is limited in space. As a result of expansion and contract of the balloon and rotation, twisting and other motions of the catheter, the wires are desired to move accordingly within the limited space. Once interference occurs between different wires during such movement, such as gathering, piling or tangling, the movement will be restricted, making the wires unable to move with expansion and contraction of the balloon and movement of the catheter any longer and prone to breakage under the action of otherwise possibly resulting forces. When this happens, temperature monitoring of the balloon surface will become impossible, and movement of the catheter will be hindered.

In view of the above, the present invention proposes a balloon catheter aiming to overcome the drawbacks of the aforementioned patent application. However, those skilled in the art would appreciate that, although embodiments of the present invention employ temperature-sensing elements arranged in an interlayer space of a double-layered balloon, which are similar to those disclosed in Patent Publication No. CN109646106 B in the name of the present applicant, they are not limited to being implemented by the arrangement of the temperature-sensing elements in the interlayer space disclosed in the patent. Those skilled in the art would also appreciate that balloons applicable to embodiments of the present invention are not limited to double-layered balloons, and the temperature-sensing elements in embodiments of the present invention are not limited to being arranged on the balloon and may be instead arranged on a section of a catheter body extending within the balloon. In other words, the balloon catheter proposed in the present invention seeks to solve the aforementioned problems arising from a relatively great number of wires received in the cavity of the catheter body, without being limited any particular locations or manner in which the temperature-sensing elements are arranged. The above-discussed structure of the balloon catheter is merely one embodiment of the present invention for solving the problems, and the present application is not limited to any particular type or material of the balloon, any particular structural arrangement of the catheter body, or the like.

Specifically, the balloon catheter proposed in the present invention includes: a catheter body; a balloon disposed at a distal end of the catheter body; a temperature-sensing element including a wire and a temperature-sensing module, the temperature-sensing module disposed on the balloon or the catheter body, the wire partially arranged in a cavity of the catheter body so as to extend in an axial direction of the cavity of the catheter body; and a restricting member disposed in the cavity of the catheter body and configured to restrict the wire of the temperature-sensing element in the cavity of the catheter body. In some embodiments, the wire of the temperature-sensing element is movable relative to the restricting member so that it will not be broken due to limited mobility during expansion or contraction of the balloon. In other embodiments, the wire of the temperature-sensing element is fixed relative to the restricting member. For example, an annular ring may be disposed over the wire, and a plurality of such annular rings may be connected in series to form a ring-shaped structure. Each adjacent two of the annular rings may be connected by a linear-shaped elastomer, and such elasticity between adjacent annular rings can resist a certain degree of tension during expansion or contraction of the balloon. In this case, breakage of the wire will not take place even when it is fixed to the annular ring.

In the balloon catheter of the present invention, through restricting and protecting the wire of the temperature-sensing element by the restricting member, problematic gathering, piling, tangling and other interference between different wires can be avoided, ensuring necessary free mobility of the wire within the cavity of the catheter body and preventing the risk of its breakage due to an otherwise possibly resulting force. Moreover, hindered movement of the catheter body (a core rod and/or an outer tube thereof) due to gathering, piling, tangling and other interference between wires can be avoided, reducing surgical complexity.

In one embodiment, the catheter body includes an outer tube and a core rod disposed in the outer tube. The core rod distally protrudes out of the outer tube, and an annular cavity is defined between the outer tube and the core rod. A distal end of the balloon is connected to the core rod, and a proximal end of the balloon is connected to the outer tube. The cavity of the catheter body includes the annular cavity, and the restricting member is disposed in the annular cavity.

In a preferred embodiment of the present invention, the balloon is preferentially a double-layered balloon including an inner balloon layer and an outer balloon layer surrounding the inner balloon layer. A distal end of the double-layered balloon is connected to the core rod, and a proximal end of the double-layered balloon is connected to the outer tube.

In a preferred embodiment of the present invention, a plurality of temperature-sensing elements are included. In some embodiments, the temperature-sensing modules of the temperature-sensing elements are disposed in an interlayer space between the inner balloon layer and the outer balloon layer. For example, they may be provided on an outer surface of the inner balloon layer, or on an inner surface of the outer balloon layer. In other embodiments, the temperature-sensing modules of the temperature-sensing elements are arranged on the catheter body (core rod) within the inner balloon layer. In other embodiments, some of the temperature-sensing modules are disposed in the interlayer space, and the other temperature-sensing modules are arranged on the catheter body (core rod) within the inner balloon layer. In case of the temperature-sensing modules being arranged in the interlayer space, e.g., on the outer surface of the inner balloon layer, or on the inner surface of the outer balloon layer, they may be configured to be able to displace relative to the inner balloon layer or the outer balloon layer. In this way, they will neither affect expansion and contraction of the balloon, nor will be broken when excessively stretched.

The balloon catheter of the present invention will be further described with reference to the accompanying drawings and preferred embodiments. The balloon catheter of the present invention is not limited to being implemented as an ablation catheter and may be instead implemented as a mapping catheter or another catheter requiring balloon surface temperature monitoring. Although the following description is set forth in the exemplary context of a double-layered balloon and an ablation catheter for illustrative purpose, this is not intended to limit the present invention in any sense, and the present invention is further applicable to single-layered balloon and balloon catheters for other uses.

Figure 2:
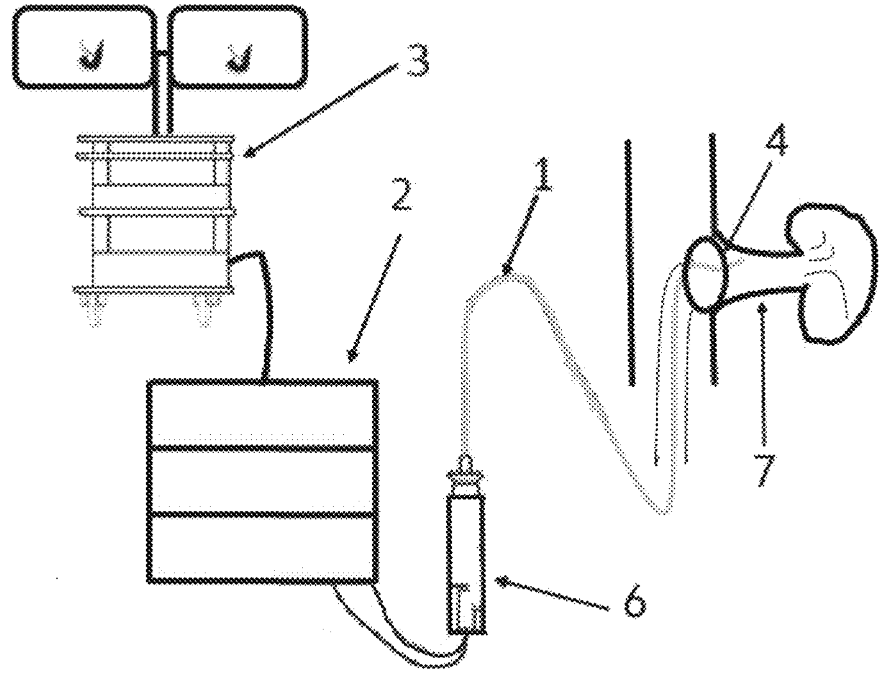
FIG. 2 schematically illustrates renal artery ablation performed with an ablation system according to a preferred embodiment of the present invention.

FIG. 1 schematically illustrates cardiac ablation performed with an ablation system according to a preferred embodiment of the present invention. FIG. 2 schematically illustrates renal artery ablation performed with an ablation system according to a preferred embodiment of the present invention.

As shown in FIGS. 1 and 2, an ablation system according to embodiments of the present invention includes an ablation catheter 1, an ablation energy output device 2 and a control device 3. The ablation energy output device 2 is brought into fluid communication with the ablation catheter 1 so as to be able to provide an ablation medium to the ablation catheter 1. In some embodiments, the control device 3 is connected to the ablation energy output device 2, which is in turn connected to the ablation catheter 1. In other embodiments, the control device 3 may be connected to both the ablation energy output device 2 and the ablation catheter 1. In further embodiments, the control device 3 may be integrated along with the ablation energy output device 2 within a single unit. However, the present invention is not limited thereto. The control device 3 functions principally to control the ablation energy output device 2 to adjust a temperature of the ablation medium (e.g., a cryogenic liquid) based on temperature information detected by the temperature-sensing element to maintain a surface temperature of the double-layered balloon within a predefined ablation temperature range. Suitable applications of the ablation system may include, but are not limited to, cryoablation of target tissue. Non-limiting examples of the target tissue may include the heart or a renal artery.

For example, as shown in FIG. 1, the ablation system may be used in a cardiac therapy, in which the ablation catheter 1 is inserted into the heart using an interventional technique in order to perform ablation of the pulmonary vein 5 for treating a cardiac arrhythmia. Alternatively, as shown in FIG. 2, the ablation system may be applied to a renal artery, wherein the ablation catheter 1 is placed at the ostium 4 of the renal artery 7 using an interventional technique in order to perform ablation of the renal artery 7 for decreasing blood pressure therein.

Figure 3:
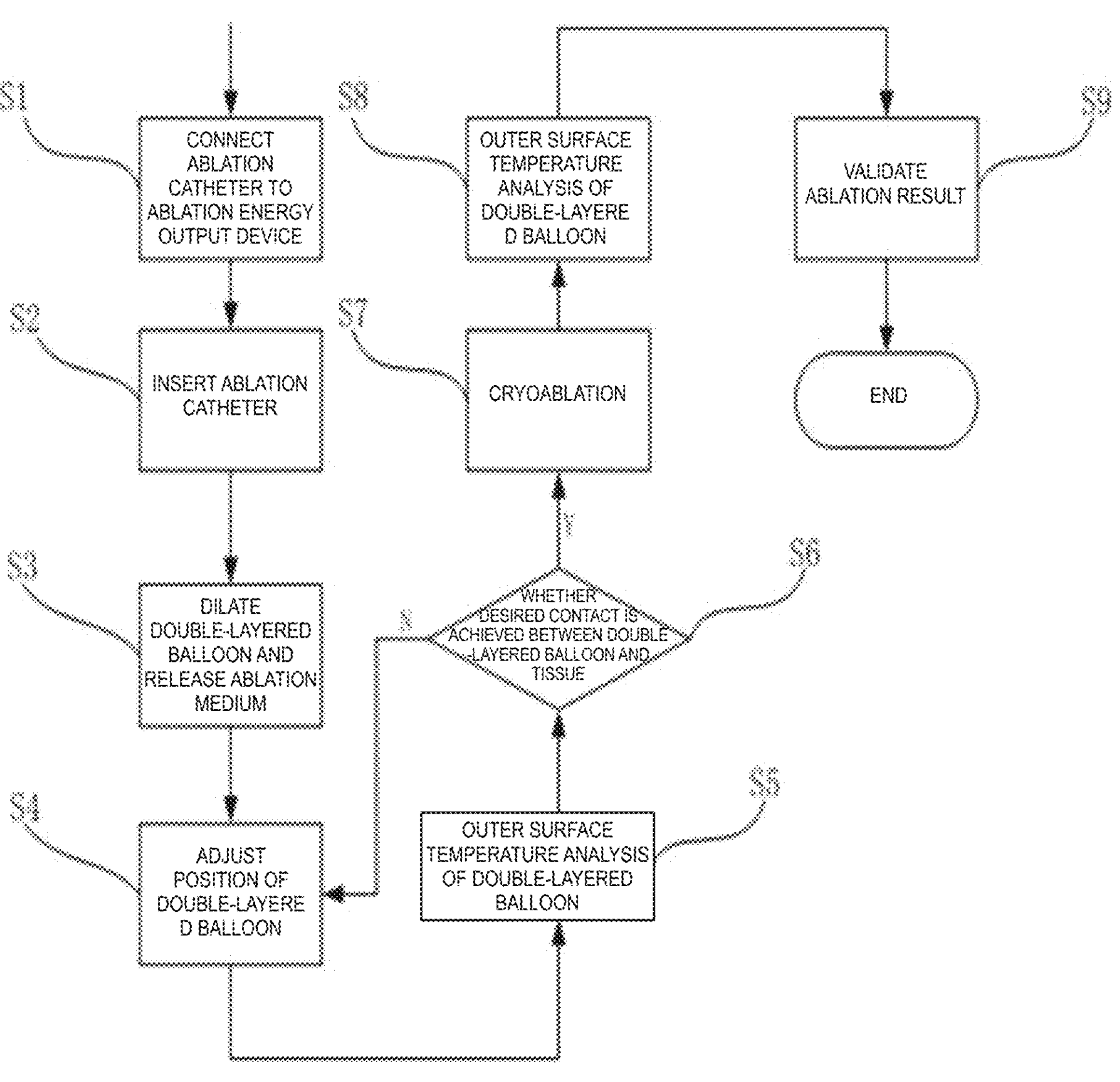
FIG. 3 is a flow diagram of operation of an ablation system according to a preferred embodiment of the present invention.

With reference to FIG. 3, the working principles of the ablation system will be further explained below with reference to its exemplary use for performing a pulmonary vein cryoablation procedure, which includes the steps as follows:

S1: Before cryoablation, connecting a control handle 6 for the ablation catheter 1 to the ablation energy output device 2.

S2: Inserting the ablation catheter 1 into the target tissue to be ablated, e.g., the pulmonary vein orifice, which is a cylindrical tissue in the heart.

S3: Dilating a double-layered balloon 20 disposed at a distal end of the ablation catheter 1 and releasing a cryogenic liquid into the double-layered balloon 20.

S4: Adjusting a position of the double-layered balloon 20 within the cylindrical tissue.

S5: Performing outer surface temperature analysis of the double-layered balloon 20 based on temperature information detected by the temperature-sensing element.

S6: Determining a contact condition of the double-layered balloon 20 with the cylindrical tissue. If desirable contact has been attained between the double-layered balloon 20 and the cylindrical tissue, the process proceeds to the next step. Otherwise, it loops back to S4.

S7: Starting cryoablation.

S8: Performing outer surface temperature analysis of the double-layered balloon 20 based on temperature information detected by the temperature-sensing element, validating the effect of cryoablation.

S9: Validating cryoablation outcomes. Specifically, cryoablation outcomes are assessed based on a variation profile of pulmonary vein potential during the cryoablation procedure. If the cryoablation outcomes are not satisfying, cryoablation may be repeated until desirable tissue ablation outcomes are obtained.

S10: Ending the ablation procedure.

In the procedure, the control device 3 analyzes and determines a contact condition between the double-layered balloon 20 and the target tissue based on temperature information detected by the ablation catheter 1 and controls, on the basis of the determination, the ablation energy output device 2 to adjust an ablation temperature of the ablation medium.

The control device 3 may include a cryogenic control unit. The ablation energy output device 2 may include a cryogenic unit, a fluid source and a fluid outlet channel. The fluid source may communicate with the fluid outlet channel so as to allow a fluid to be output from the fluid source to the ablation catheter 1 through the fluid outlet channel. For example, the fluid outlet channel may be connected to a fluid inlet interface on the control handle 6 so as to introduce the ablation medium to the ablation catheter 1. The cryogenic unit may be provided on the fluid outlet channel in order to cool the fluid flowing through the fluid outlet channel. The cryogenic unit may be a compressor or another type of cooling device, and the present invention is not limited to any particular structure that it employs. The cryogenic unit may be communicatively connected to the cryogenic control unit and operate under the control thereof. More specifically, the cryogenic control unit may control, based on a received cryoablation command, the cryogenic unit to operate to supply the cryogenic liquid to the ablation catheter 1 through the fluid outlet channel. In embodiments of the present invention, a cryoablation button may be provided on the control handle 6, or a graphic representation thereof may be provided on a computer interface. In such cases, a cryoablation command may be launched to the cryogenic control unit when the operator activates the button or graphic representation thereof. The computer interface may be provided on the control device 3 or on the ablation energy output device 2. As a non-limiting example, the cryogenic control unit may issue a signal indicating a cryogenic request to the cryogenic unit, and the cryogenic unit may deliver cryogenic energy upon receiving the signal.

During cryoablation, the cryogenic control unit may control, based on temperature information from a plurality of temperature sensing elements, the cryogenic unit to adjust a level of cryogenic energy it delivers so as to maintain the balloon's outer surface temperature within a predetermined cryoablation temperature range.

Figure 4:
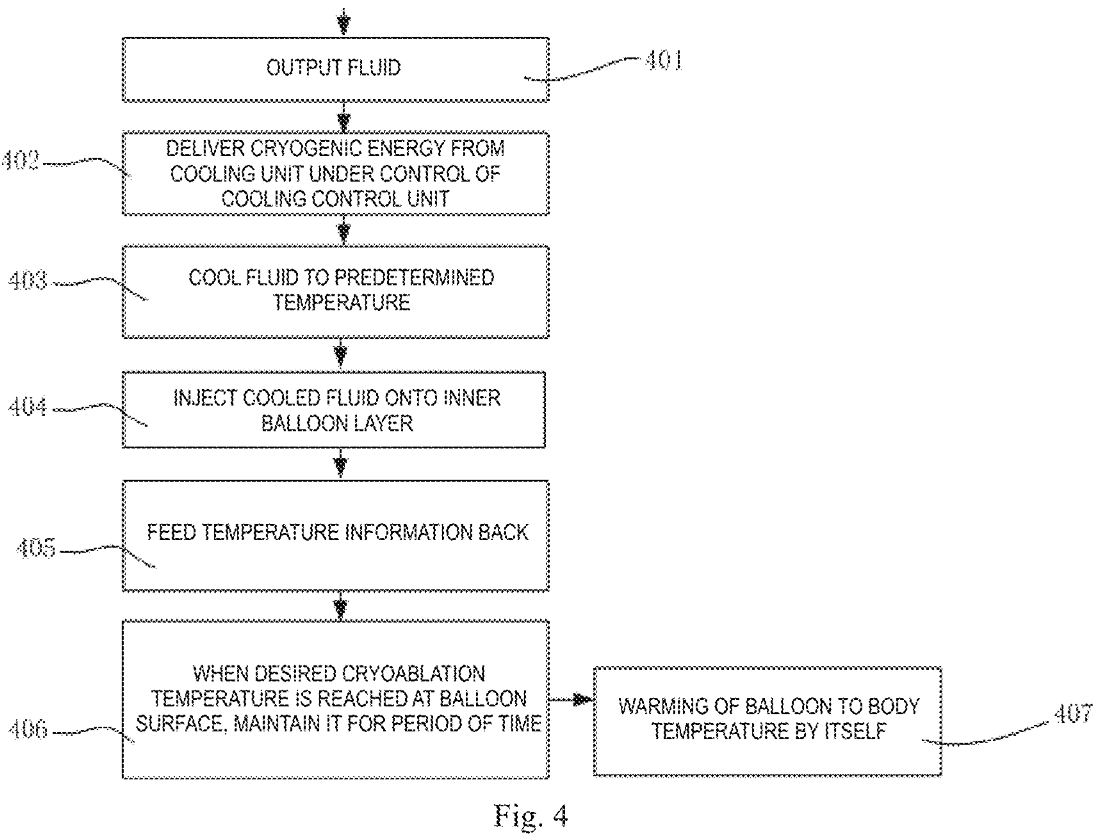
FIG. 4 is a flowchart of a cryoablation procedure performed by an ablation system according to a preferred embodiment of the present invention.

More particularly, as shown in FIG. 4, a cryoablation procedure performed by the ablation system may include the steps as follows:

401: Outputting a fluid from the fluid source to the fluid outlet channel.

402: Controlling, by the cryogenic control unit, the cryogenic unit to deliver cryogenic energy.

403: Cooling the fluid to a predetermined temperature;

404: Injecting the cryogenic liquid to the inner balloon layer. Steps 401, 402, 403 and 404 may be carried out simultaneously so that the cryogenic liquid is injected onto an inner surface of the balloon at the beginning of cooling.

405: Controlling cryogenic energy from the cryogenic unit in real time by the cryogenic control unit based on temperature information from the temperature sensing element.

406: Ending the procedure after a desired cryoablation temperature (e.g., from −40° C. to −60° C.) has been reached at the balloon surface and maintained for a period of time (e.g., 120-180 seconds).

Following the completion of this cryoablation procedure, the physician may evaluate the cryoablation quality and determine whether another cryoablation cycle is necessary. However, it would be appreciated that each subsequent cryoablation cycle can be initiated only after the double-layered balloon warms to the body temperature by itself (step 407).

Figure 5:
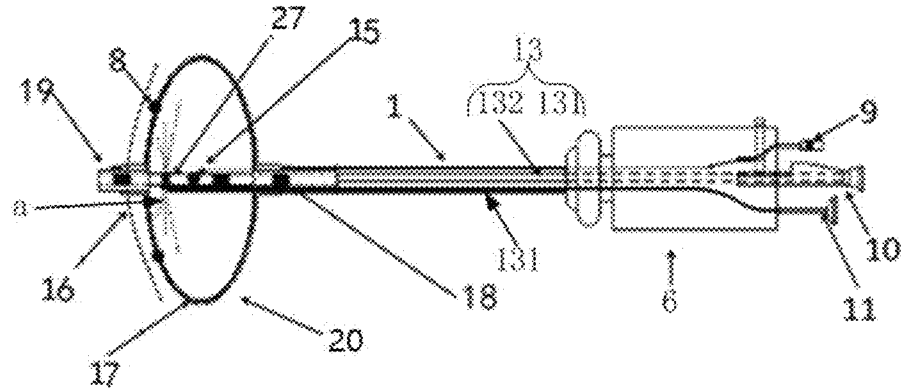
FIG. 5 is a front view of an ablation catheter according to a preferred embodiment of the present invention.
Figure 6:
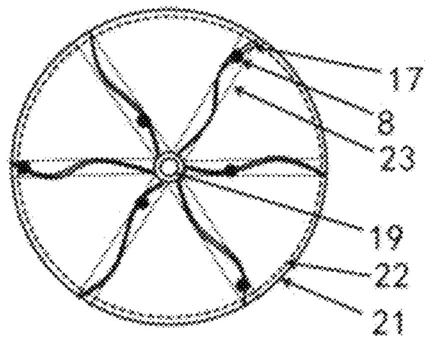
FIG. 6 is a left view of the ablation catheter of FIG. 5.
Figure 8:
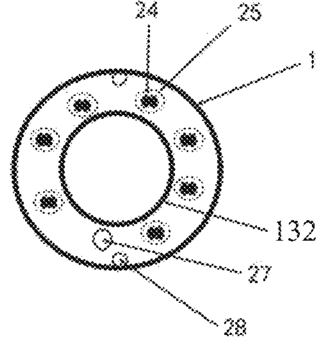
FIG. 8 is a schematic illustration of an end face of a catheter body in an ablation catheter according to a preferred embodiment of the present invention.
Figure 10:
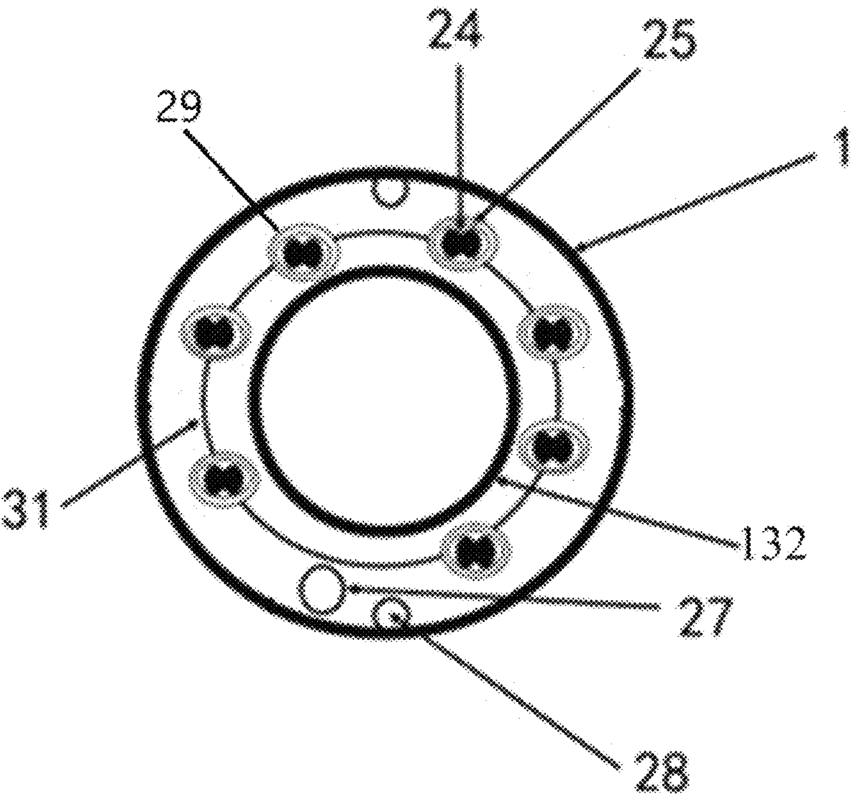
FIG. 10 schematically illustrates how first restricting members restrict wires of all temperature-sensing elements in a cavity of a catheter body according to a preferred embodiment of the present invention, wherein the first restricting members are disposed thereover with second restricting members which are connected to form a ring-shaped structure.

The ablation catheter 1 is preferably structured as shown in FIGS. 5 and 6, in conjunction with FIGS. 8 and 10. As shown, the ablation catheter 1 includes a double-layered balloon 20, a first temperature-sensing element 17, a catheter body 13, a securing member 23 and a fluid inlet tube 27. The double-layered balloon 20 is disposed at a distal end of the catheter body 13 in such a manner that part of the catheter body 13 is received in the double-layered balloon 20. The catheter body 13 includes an outer tube 131 and a core rod 132. The core rod 132 is disposed within the outer tube 131 so as to distally protrude out of the outer tube 131 and be connected to a distal end of the double-layered balloon 20. The double-layered balloon 20 is connected at a proximal end thereof to the outer tube 131. A distal end of the fluid inlet tube 27 is placed inside the double-layered balloon 20 and threadedly engaged with the core rod 132. The fluid inlet tube 27 is configured to inject an ablation medium to the double-layered balloon 20. Examples of the ablation medium may include, but are not limited to, a cryogenic liquid. An annular cavity is defined between the core rod 132 and the outer tube 131.

The double-layered balloon 20 includes an outer balloon layer 21 and an inner balloon layer 22. The outer balloon layer 21 surrounds the inner balloon layer 22. The outer balloon layer 21 and the inner balloon layer 22 are fixed at both proximal and distal ends thereof to the catheter body 13. Both the outer balloon layer 21 and the inner balloon layer 22 are expandable. For example, when a cryogenic liquid is injected from a distal end of the fluid inlet tube 27 into an inner cavity delimited by the inner balloon layer 22, it will be instantly vaporized by heat absorbed from a patient's tissue. As a result, expansion of the inner balloon layer 22 will occur, which will in turn cause expansion of the outer balloon layer 21.

The first temperature-sensing element 17 includes a wire 24 and a temperature-sensing module. Typically, two wires 24 are included, for example, parallel Cu and CuNi wires. The Cu and CuNi wires may be connected to each other at a particular site of the balloon, and the temperature-sensing module may be formed by the connection (i.e., a temperature measurement point 8, see FIGS. 5 to 7). The temperature-sensing module is configured to sense a temperature and produce information about the temperature. The temperature-sensing module is also configured to convert the temperature information into electrical information, which is led out through the wires. At least one such first temperature-sensing element 17 may be included, with the temperature-sensing module(s) thereof being disposed in an interlayer space defined between the inner balloon layer 22 and the outer balloon layer 21 (not shown). Since the temperature-sensing module of the first temperature-sensing element 17 is able to detect temperature information of an area to be ablated 16 in the vicinity of the first temperature-sensing element 17, through arranging the temperature-sensing module of the first temperature-sensing element 17 in the interlayer space between the inner balloon layer 22 and the outer balloon layer 21, which is close to an outer surface of the double-layered balloon 20, accurate temperature information of the outer surface of the double-layered balloon 20 can be estimated from the temperature information detected by the first temperature-sensing element 17, resulting in improved ablation outcomes. In addition, the first temperature-sensing element 17 is attached to the inner balloon layer 22 or the outer balloon layer 21 by the securing member 23. For example, in FIG. 7, the first temperature-sensing element 17 is attached to an outer surface of the inner balloon layer 22 or an inner surface of the outer balloon layer 21 by the securing member 23, thereby enabling the temperature-sensing module of the first temperature-sensing element 17 to monitor a temperature at a designated position on the double-layered balloon 20. Further, in order to enable the first temperature-sensing element 17 to accommodate expansion and contraction of the double-layered balloon 20, the securing member 23 may have attachment or other suitable ability, which allows the securing member 23 to displace relative to the double-layered balloon 20 in response to deformation of the material at the balloon surface where it is anchored during expansion or contraction of the double-layered balloon 20. As the first temperature-sensing element 17 is attached to the inner balloon layer 22 or the outer balloon layer 21 by the securing member 23, it is also able to displace relative to both the double-layered balloon 20 and the securing member 23. In a preferred embodiment of the present invention, the securing member 23 is physically attached to the first temperature-sensing element 17 and the balloon surface in the same manner as described in Patent Publication No. CN109646106 B in the name of the present applicant. Further detailed description thereof is therefore considered unnecessary.

Figure 7:
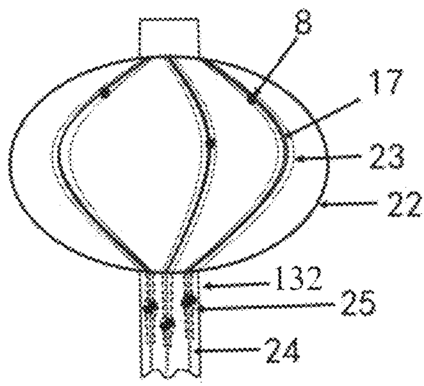
FIG. 7 is a schematic illustration of a distal end of an ablation catheter according to a preferred embodiment of the present invention.

Reference is now made to FIGS. 6 and 7. Preferably, a plurality of (as used herein, this term means "at least two") first temperature-sensing elements 17 are provided, with their temperature-sensing modules scattered at different positions in the interlayer space. Preferably, they are circumferentially uniformly distributed about a center axis of the inner balloon layer 22. In this way, a plurality of temperature measurement points 8 may be established, each by the temperature-sensing module of a respective one of the first temperature-sensing elements 17. In this embodiment, with the plurality of first temperature-sensing elements 17, temperature information at a plurality of positions can be detected. Although six temperature measurement points 8 are shown in FIG. 6, the present invention is not so limited, and more or fewer temperature measurement points 8 may be alternatively provided. Further, the first temperature-sensing elements 17 may be linear-shaped sensors, such as thermocouple- or thermistor-based temperature sensors. That is, the temperature-sensing modules may be regular thermocouples, such as T- or K-type thermocouples, or thermistors. Each wire 24 in the first temperature-sensing elements 17 may be partially disposed in the cavity of the balloon, and the rest may be disposed in the annular cavity between the outer tube 131 and the core rod 132 so as to extend in the axial direction of the annular cavity. Moreover, each wire 24 in the first temperature-sensing elements 17 may be proximally connected to an electrical input/output interface 9 on the control handle 6, thereby enable output of the detected temperature information.

It would be appreciated that, in addition to the temperature-sensing module or modules arranged in the interlayer space of the double-layered balloon 20, one or more other temperature-sensing modules may be provided at different locations. For ease of differentiation, hereinafter, any temperature-sensing element 17 with its temperature-sensing modules being arranged in the interlayer space of the double-layered balloon 20 is referred as a first temperature-sensing element 17, and any temperature-sensing element with the temperature-sensing module being disposed at a different location as a second temperature-sensing element. For example, as shown in FIG. 5, at least one second temperature-sensing element 15 may be provided, with its temperature-sensing module being arranged on a section of the core rod 132 extending in the double-layered balloon 20, in order to capture temperature information of the interior of the balloon. Moreover, the temperature-sensing module of the second temperature-sensing element 15 may also be connected by a wire 24 to an electrical input/output interface 9 on the control handle 6. Of course, different temperature-sensing elements may be connected to the same electrical input/output interface 9, which may include multiple data channels for transmitting data from or to the temperature-sensing elements.

In a preferred embodiment of the present invention, at least one first temperature-sensing element 17 is provided with its temperature-sensing module being arranged in the interlayer space of the double-layered balloon 20, and at least one second temperature-sensing element 15 is provided with its temperature-sensing module being arranged on the section of the core rod 132 in the balloon. Preferably, a plurality of first temperature-sensing elements 17 are provided. Restriction of the wires 24 of the temperature-sensing elements in the annular cavity will be described below in the exemplary context of six first temperature-sensing elements 17 and one second temperature-sensing element 15. In this embodiment, each of the temperature-sensing elements (e.g., first 17 and second 15 temperature-sensing elements) includes one temperature-sensing module and a set of wires 24 (generally consisting of two wires 24).

With continued reference to FIGS. 5 to 7, the temperature-sensing modules of the six first temperature-sensing elements 17 may be arranged on the outer surface of the inner balloon layer 22, and the temperature-sensing module of the one second temperature-sensing element 15 may be arranged on the core rod 132. Each of the wires 24 of the six first temperature-sensing elements 17 and the one second temperature-sensing element 15 may be partially arranged in the annular cavity between the core rod 132 and the outer tube 131, and the rest may be disposed in the cavity of the balloon. For given dimensions of the core rod 132 and the outer tube 131, more wires 24 are associated with an increased risk of limited mobility within the annular cavity. In order to overcome this problem, at least some of the wires 24 of the temperature-sensing elements are provided thereover with restricting members for restricting these wires 24 so that the wires 24 of the multiple temperature-sensing elements are separated or spaced apart from one another without interference (e.g., gathering, tangling, etc.) in the annular cavity. The wires 24 are so restricted by the restricting members as to be either movable or stationary relative to the restricting members, without departing from the scope of the present invention. By doing so, the restricting members can avoid interference of the wires 24 with one another, ensuring their free mobility which avoids their breakage under the action of otherwise possibly resulting forces. Moreover, the wires 24 can be avoided from hindering movement of the core rod 132 and/or the outer tube 131.

In some embodiments, as many restricting members as the number of temperature-sensing elements are provided in such a manner that they are spaced apart from one another in the annular cavity. Moreover, the wires 24 of the temperature-sensing elements are passed through the respective restricting members. In this way, the wires 24 of all the temperature-sensing elements are restricted and protected by the restricting members so as to be separated from one another within the annular cavity, effectively circumventing the problem of interference of different wires 24.

In other embodiments, the number of restricting members is at least one and less than that of temperature-sensing elements. In this case, only the wires 24 of some of the temperature-sensing elements are passed through the restricting members, each through one of the restricting members. Moreover, the wires 24 restricted by the restricting members may not be adjacent ones. In these embodiments, not all, but only some non-adjacent ones, of the wires 24 in the temperature-sensing elements are restricted. In this way, multiple wires 24 can be separated or spaced apart from one another to avoid interference of them, while minimizing the occupation of the limited space by the restricting members.

Further, when each of the wires 24 in the temperature-sensing elements is restricted by a separate restricting member, preferably, at least adjacent restricting members are staggered in the axial direction of the annular cavity (i.e., they are not located on the same circumferences). This can avoid interference of the multiple restricting members.

Further, the restricting members may be either fixed in position or movable within the annular cavity. In the former case, they may be fixedly connected to an inner wall surface of the outer tube 131, or to an outer wall surface of the core rod 132. Alternatively, the restricting members may extend to a proximal end of the catheter body 13 and fixedly connected to the control handle 6. The present invention is not limited to any particular manner in which the restricting members are fixed.

Further, it would be appreciated that in order to enable restriction of the wires 24, the restricting members may define restriction channels extending axially therethrough, and the wires 24 of the temperature-sensing elements can be restricted simply by inserting them through the restriction channels. This can provide structural simplicity and allows the restricting members to be arranged in the limited space. In this embodiment, the restriction channels may completely surround the wires 24 along with the inner wall surface of the outer tube 131. That is, the restriction channels may be designed to be circumferentially open, or as circumferentially closed bores. In the latter case, the restriction channels can fully surround the wires 24 by themselves. The present invention is not limited to any particular length across which the wires 24 are surrounded by the restricting members. Portions of the wires 24 within the annular cavity may be surrounded across their entire length or part thereof. That is, the restricting member may have an axial length less than or equal to an axial length of the outer tube 131. It would be also appreciated that, herein, each temperature-sensing element may include a set of wires 24 consisting of two wires 24, which may be restricted by a single restricting member or separate restricting members.

Further, the restricting members may be designed as sleeves 25 (see FIG. 7), which may be round or oval tubes. In practical operation, the sleeves 25 can be set in place simply by disposed them over the wires 24 preferably in such a manner the wires 24 is movable relative to the sleeves 25 to better ensure that the wires 24 can be freely extended or retracted. Additionally, the sleeves 25 may be so deployed so as to movable or fixed in the annular cavity. Additionally, the wires 24 in each temperature-sensing element may be provided with a single sleeve 25 or separate sleeves 25. In the latter case, the sleeves 25 may staggered from each other in the direction in which the wires 24 extend.

The sleeves 25 may be made of a polymer material, more preferably a thermoplastic material. Examples of the thermoplastic material may include polyethylene terephthalate (PET), poly etheramide (PEBAX™) polytetrafluoroethylene (PTFE), polyimide (PI), polyamide (PA, nylon), other polymer materials and combinations thereof. In this way, the sleeves 25 can have desirable stiffness and flexibility, which can not only avoid possible damage to the wires 24, but can also separate the wires 24 in a desirable way. More preferably, the sleeves 25 are made of PET. This material can impart sufficient stiffness to the sleeves 25, which can avoid deformation of the sleeves 25 during movement of the wires 24 that may make the catheter more difficult to use, thereby facilitating use of the catheter.

Considering that the annular cavity between the outer tube 131 and the core rod 132 has small dimensions, the sleeves 25 are desirably designed with a corresponding small size. Moreover, for space-saving purpose, the sleeves 25 may be fabricated so that, when deployed, their inner wall surfaces will be tightly fitted against the sleeved wires 24. That is, an inner dimension (e.g., inner diameter) of the sleeves 25 may be equal to or slightly greater than an outer diameter of the wires 24, as long as it is ensured that the wires 24 are movable within the sleeves 25. The sleeves 25 may be glued to the outer tube 131 or the core rod 132. Alternatively, they may extend to the proximal end and fixedly connected to the control handle 6. The present invention is not limited to any particular length of the sleeves 25. For example, they may be as long as or shorter than the outer tube 131. For example, the sleeves 25 may be short and disposed around a proximal end of the double-layered balloon 20. In case of a small length of the sleeves 25, they may be directly attached to the inner wall surface of the outer tube 131. When they are so long as to extend to the control handle 6 at the proximal end, they may be attached additionally to the control handle 6.

Figure 9:
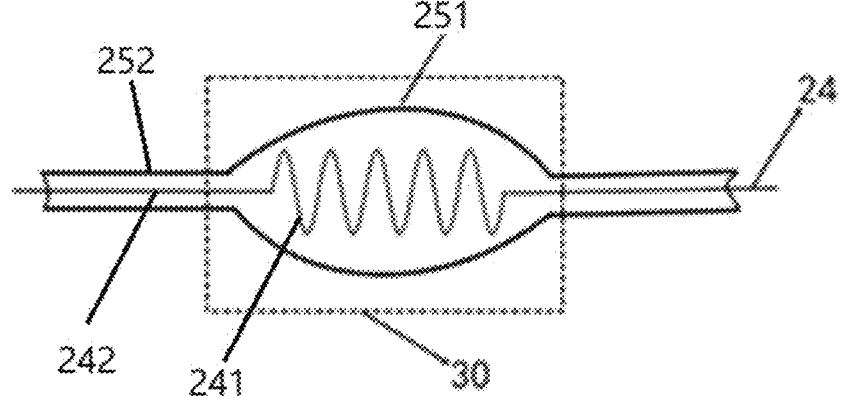
FIG. 9 is a schematic diagram illustrating part of a sleeve according to a preferred embodiment of the present invention.

Further, the wires 24 may be fabricated so as to be partially curved, for example, into a serpentine shape. Accordingly, the wires 24 may have curved portions 241 (see FIG. 9). As shown in FIG. 9, the wires 24 may each have extensions 242 and at least one curved portion 241. The extensions 242 are non-curved portions of the wires. When compressed, the curved portions 241 may assume a greater overall radial size than the extensions 242. In practice, copper wires may be partially curved into a serpentine shape while being heated, and then quenched for shape finalization. The curved portions 241 may function like springs. That is, they may be stretched and elongated, and may recoil after the external force is removed. Thus, the curved portions 241 impart to the wires 24 certain mobility margins for elongation and compression, which can prevent their breakage during movement of the catheter or during expansion or contraction of the balloon. Preferably, when compressed (i.e., the configuration as indicated by the dotted box 30 in FIG. 9), the curved portions 241 may have an axial length of 2 mm to 5 mm. Additionally, the wires 24 may be overall elongated by an amount that does not exceed 60% of an outer diameter of the inner balloon layer 22 being in a dilated and expanded configuration. In this embodiment, the wires 24 of the first temperature-sensing elements 17 are distally arranged on a domed portion of the double-layered balloon 20. With this dimensional arrangement, during a transition of the balloon from a collapsed configuration to the expanded configuration, the mobility margins of the wires 24 allows their elongation or compression with the expansion or contraction of the balloon. A large elongation amount of the wires 24 is considered unnecessary because it may lead to not only additional occupation of the limited space of the cavity of the catheter body but also tangling of the wires 24. The present invention is not limited to any particular number and locations of the curved portions 241, and the curved portions 241 may be located anywhere on the wires 24, for example, in proximity to the proximal end of the balloon or to the control handle 6, or anywhere between the proximal end of the balloon and the control handle 6.

With continued reference to FIG. 9, the sleeves 25 are preferred to each have narrower portions 252 and at least one broader portion 251 (one broader portion 251 is encircled by the dotted box 30 in FIG. 9). The narrower portions 252 each have a luminal cross-sectional area smaller than a luminal cross-sectional area of the broader portion 251. The broader portions 251 are adapted to accommodate, and thus restrict and protect, the curved portions 241 of the wires 24. As a result, tangling of the curved portions 241 of different wires during expansion or contraction of the balloon or during movement of the catheter can be avoided, additionally mitigating the problem of interference of the wires and reducing their risk of breakage due to otherwise possibly resulting forces. Moreover, the narrower portions 252 are adapted to accommodate the extensions 242 of the wires 24. A maximum outer dimension (outer diameter) of the broader portions 251 is smaller than a width of the annular cavity between the outer tube 131 and the core rod 132. This configuration can ensure mobility of the curved portions 241 during expansion or contraction of the balloon, additionally ensuring that the wires 24 will not be broken due to otherwise possibly resulting forces. In some embodiments, as many sleeves 25 as the number of temperature-sensing elements are provided. In these cases, the sleeves 25 may be spaced apart from one another within the annular cavity, and the wires 24 of the temperature-sensing elements may be movably inserted through the respective sleeves 25. Additionally, it is preferred that the broader portions 251 of the sleeves 25 over the wires 24 of at least adjacent ones of the temperature-sensing elements are staggered from each other in the axial direction of the annular cavity (i.e., they are not located on the same circumferences of the core rod 132). In this way, the risk of interference between the sleeves 25 can be reduced. Alternatively, the number of sleeves 25 may be at least one and smaller than that of temperature-sensing elements. In this case, only the wires 24 of some of the temperature-sensing elements are movably inserted through the sleeves 25, each through one of the sleeves 25. Moreover, the sleeved wires 24 may not be adjacent ones. Alternatively, the broader portions 251 of the sleeves 25 over the wires 24 of at least adjacent ones of the temperature-sensing elements may be staggered from each other in the axial direction of the annular cavity.

During assembly, the sleeves 25 may be set in place simply by disposing them over the curved portions 241 of wires 24 in the temperature-sensing elements so that the curved portions 241 are received in the broader portions 251 of the sleeves 25. Additionally, in order to reduce material cost, the sleeves 25 are preferably designed with a short axial length of, for example, 10 mm to 20 mm. Moreover, they are preferably disposed proximate the proximal end of the balloon. In addition to lower cost, this dimensional design can ensure that the curved portions 241 of the wires are situated in the broader portions 251 of the sleeves 25, avoiding interference of the wires 24.

The present invention is not limited to any particular shape of the sleeves 25. Apart from the oval and round shapes enumerated above, other shapes are also possible, including regular shapes such as circular and rectangular and irregular shapes.

With additional reference to FIG. 8, as an example, six first temperature-sensing elements 17 and one second temperature-sensing element 15, a total of seven temperature-sensing elements, are arranged on the balloon catheter. Preferably, at least one sleeve 25 is disposed over the wires 24 of each temperature-sensing element. The sleeves 25 over the wires 24 may be arranged circumferentially around the annular cavity either evenly or not, or even arbitrarily within the annular cavity. In the annular cavity, there are generally other lumens or wires, such as the fluid inlet tube 27 and traction thread tubes 28. There may be two traction thread tubes 28, through which traction threads for controlling distal bending deformation of the balloon catheter may be passed.

Further, the ablation catheter 1 may include a plurality of restricting members. For example, the restricting members may be implemented as sleeves 25. These sleeves 25 may be arranged circumferentially around an axis of the core rod 132 and spaced apart from one another. Preferably, these sleeves 25 are connected in series to form a ring-shaped structure. That is, in some embodiments, the circumferentially-arranged sleeves 25 may not be connected together and independent of one another. However, in alternative embodiments, the circumferentially-arranged sleeves 25 may be connected together to form a ring-shaped structure. It would be appreciated that, in the latter cases, the sleeves 25 are movably disposed in the annular cavity and connected together. Additionally, one or more such ring-shaped structures may be provided. In the latter case, the ring-shaped structures may be spaced apart along the axial direction of the core rod 132, i.e., the direction of extension of the wires 24, in order to restrict the wires 24. In practical use, wire(s) 24 may be inserted through each of the sleeves 25 constituting the ring-shaped structure(s), and the number of sleeves 25 in each ring-shaped structure may be less than or equal to the number of temperature-sensing elements. In this way, only the wires 24 of some of the temperature-sensing elements may be restricted by the sleeves 25, or the wires 24 of all the temperature-sensing elements may be restricted by the sleeves 25. Here, it would be appreciated that the ring-shaped structure(s) may be elastic and deformable accordingly with movement of the sleeves 25 or the wires 24. In this way, the ring-shaped structure(s) will not hinder movement of the catheter or expansion or contraction of the balloon, and can act to avoid interference of the sleeves 25. In this case, the wires 24 in the sleeves 25 are preferably movable relative to the sleeves 25.

Figure 11:
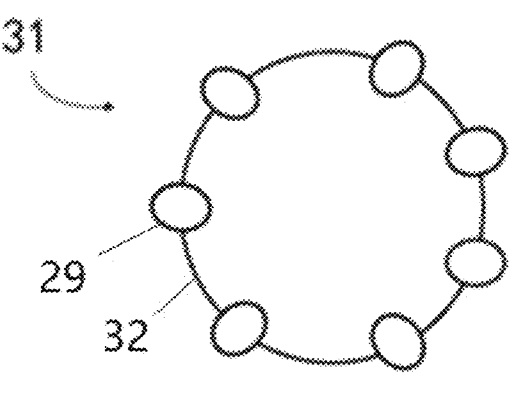
FIG. 11 schematically illustrates how second restricting members or restricting members are connected together to form a ring-shaped structure according to a preferred embodiment of the present invention.

In alternative embodiments, as shown in FIG. 11, each restricting member may be designed as a ring-shaped structure 31 with annular rings 29. The ring-shaped structure 31 may be so formed that adjacent annular rings 29 are connected by linear-shaped elastomers 32. The wires 24 of the temperature-sensing elements may be passed through the annular rings 29. The number of annular rings 29 may be less than or equal to the number of temperature-sensing elements. In this way, only the wires of some of the temperature-sensing elements may be restricted by the annular rings 29, or the wires of all the temperature-sensing elements may be restricted by the annular rings 29. Both the annular rings 29 and the linear-shaped elastomer 32 may be made of elastic materials, such as silicone rubber, PA, Pebax, PI, etc., but the present invention is not limited to any particular materials. One or more such ring-shaped structures 31 may be provided. In the latter case, the ring-shaped structures 31 may be spaced apart along the axial direction of the core rod 132, i.e., the direction of extension of the wires 24, in order to restrict the wires 24. Such a design can prevent interference of the wires 24 and avoid movement of the wires 24 from adversely affecting operation of components in the catheter body 13. Further, the annular rings 29 may be implemented either as annular doughnuts, or as PI tubes, without limited the present invention in any sense.

In other embodiments, the restricting members may include first restricting members and second restricting members. The second restricting members may be configured to restrict the first restricting members, while the first restricting members may be configured to in turn restrict the wires of the temperature-sensing elements 24. Specifically, the wires 24 may be inserted through the first restricting members, which may be in turn inserted through the second restricting members.

Further, in case of a plurality of first restricting members, they may be circumferentially spaced apart about the axis of the core rod 132. In this case, as many second restricting members as the number of first restricting members may be provided, and each of the first restricting members may be restricted by a respective one of the second restricting members. Alternatively, in case of a plurality of first restricting members, a plurality of second restricting members less than the plurality of first restricting members may be provided. In this case, only some of the first restricting members are restricted by the second restricting members. In embodiments, the second restricting members may be designed as annular rings 29, which are connected in series to form a ring-shaped structure 31 (see FIG. 11). Adjacent annular rings 29 may be connected by linear-shaped elastomers 32. Further, each of the annular rings 29 may be disposed therein with one of the first restricting members. Here, the first restricting members may be implemented as sleeves 25 or other suitable structures.

In a preferred embodiment of the present invention, the ablation catheter 1 includes first restricting members and second restricting members surrounding the first restricting members. As shown in FIG. 10, the first restricting members are preferably implemented as sleeves 25, and the second restricting members are preferably implemented as annular rings 29. Both the annular rings 29 and the sleeves 25 are circumferentially spaced apart about the axis of the core rod 132. The sleeves 25 are configured for passage of the wires 24 of the temperature-sensing elements therethrough and thereby restriction of the wires 24. Preferably, the wires 24 of the temperature-sensing elements are movably disposed in the sleeves 25. The sleeves 25 are in turn arranged in the annular rings 29, which connected in series to form a ring-shaped structure 31, and each adjacent two of the annular rings 29 are connected by a linear-shaped elastomer 32. Preferably, the sleeves 25 are fixed within the annular rings 29. Each annular ring 29 may consist of one or more wound filaments and may have a length that is almost ignorable compared to a length of the sleeves 25. The ring-shaped structure 31 may resemble a coil spring and retain all the sleeves 25. In practical use, the ring-shaped structure 31 may be first disposed over the core rod 132, and the sleeves 25 retaining the wires therein may be passed through the annular rings 29 on a circumference of the elastic coil. The annular rings 29 may be sized comparable to the narrower portions 252 and/or broader portions 251 of the sleeves 25. Thus, the wires 24 and sleeves 25 may be scattered and fixed around the core rod 132 in the outer tube 131.

The ring-shaped structure 31 may be made of an elastic material such as silicone rubber, PA, Pebax, PI or the like. It would be appreciated that the ring-shaped structure 31 may deform accordingly with movement of the sleeves 25 or the wires 24. The ring-shaped structure 31 is preferably made of silicone rubber because this material is easily available, highly biocompatible, strongly elastic, and safe and reliable in use. Preferably, the ring-shaped structure 31 may be restricted by its friction with the outer tube 131 and the core rod 132. Compared with gluing and the like, the use of the ring-shaped structure 31 can effectively reduce overall stiffness of the catheter at the restricting members.

Further, a plurality of ring-shaped structures 31 may be arranged side by side from the proximal end of the balloon in the ablation catheter 1 to the control handle 6 at an interval of, for example, 100 mm.

With continued reference to FIG. 5, in embodiments of the present invention, the catheter body 13 may be a non-rigid structure that is freely flexible. The catheter body 13 is preferably made of a polymer material, such as thermoplastic polyurethane (TPU) elastomer rubber, block polyetheramide resin (PEBAX™) or nylon with metal wires. Alternatively, it may be a braided metal tube. Preferably, the catheter body 13 is provided at the proximal end thereof with a control handle 6, which may be particularly configured to manipulate and control bending of the catheter body 13. The control handle 6 may be provided with an electrical input/output interface 9, and the first temperature-sensing elements 17 may be proximally passed through the catheter body 13 and connected to the electrical input/output interface 9, thus enabling transmission of detected temperature information to an external device. The control handle 6 may further include at least one fluid interface 11 and at least one lumen access interface 10. The lumen access interface 10 may be configured to introduce a guidewire, a mapping catheter, a contrast medium or other instruments. The fluid interface 11 may be brought into fluid communication with the fluid inlet tube 27 in order to introduce an ablation medium from an external source into the ablation catheter 1. It may be further configured to discharge the ablation medium or other media from the double-layered balloon 20. The distal end of the fluid inlet tube 27 may be disposed within the inner balloon layer 22, thus enabling injection of the ablation medium onto the inner surface of the inner balloon layer 22. Further, the fluid inlet tube 27 may in particular include a distal spiral structure and a longitudinal extension in fluid communication with the spiral structure. The longitudinal extension may be passed through the catheter body 13 and connected to the fluid interface 11. Multiple fluid injection ports may be provided in the spiral structure in order to inject the ablation medium a in various directions.

The control handle 6 may be provided on the outer tube 131, and the fluid inlet tube 27 and the core rod 132 may be inserted through the outer tube 131 side by side. The core rod 132 may be a hollow structure movably disposed in the outer tube 131. The control handle 6 may be manipulated to cause the core rod 132 to move within the outer tube 131 to enable release from a sheath, retraction into the sheath and withdrawal therein, of the double-layered balloon 20. The core rod 132 may be proximally brought into communication with the lumen access interface 10 in the control handle 6, thereby allowing passage of a necessary instrument therethrough, such as a guidewire, a mapping catheter or a contrast fluid. In practical use, a fluid discharge pipe may be disposed between the core rod 132 and the outer tube 131. At the distal end of the core rod 132 that is located out of the double-layered balloon 20, a soft tip 19 made of a soft material is preferably provided to avoid causing damage to any tissue that it comes into contact. Preferably, a radiopaque marker 18 made of a metallic, radiopaque material is disposed at the distal end of the core rod 132. During a procedure, the radiopaque marker 18 can be detected by a fluoroscopic imaging device, helping a physician confirm the position of the double-layered balloon 20 relative to an outer sheath.

At last, although several preferred embodiments of the present invention have been described above, the scope of the invention is in no way limited to these embodiments. For example, the restricting members are not limited to being implemented as tubular structures surrounding the wires. For example, they may alternatively be implemented as spiral bands wrapping around the wires, or as annular coils surrounding the wires. Therefore, the present invention is not limited to any particular manner in which the wires are surrounded by the restricting members, as long as the multiple wires can be separated from one another. The various embodiments of the present application can be implemented in combination. For example, the wires may have curved portions, and the sleeves may have broader portions, wherein the curved portions are accommodated in the broader portions; the sleeves are arranged circumferentially around the axis of the core rod and provided thereover with annular rings for restricting the sleeves; and adjacent annular rings are connected to form a ring-shaped structure. Other examples are also possible, without departing from the scope of the present application.

Although the innovation of the present invention comes out from the field of electrophysiological balloon catheters and ablation system thereof, those skilled in the art would appreciate that the present invention can also be applied to catheters used in other fields, such as catheters with multiple fingers each provided thereon with several electrodes. As needed, such catheters can provide bending control for diagnosis and treatment. However, during bending control, wires connecting the electrodes are prone to stretching and breakage, or to tangling within a cavity of the catheter, which is detrimental to the use of the catheter. The above-described technique can be employed to overcome these problems. As another example, balloon RF ablation catheters with several electrodes and sensors arranged on a balloon thereof can be used for diagnosis, treatment or monitoring of tissue conditions. Similarly, wires connecting the electrodes and sensors on the balloon are prone to breakage, tangling within a cavity of the catheter or other problems during expansion or contraction of the balloon. The above-described technique can be employed to overcome these problems. Indeed, the concept of the present invention can be used in any application associated with the problem of interference or breakage of wires due to tangling, but some structural adaptations may be necessary.

The foregoing description presents merely preferred embodiments of the present invention and is not intended to limit the scope of the present invention in any way. Any and all changes and modifications made by those of ordinary skill in the art in light of the above teachings without departing from the spirit of the present invention are intended to be embraced in the scope as defined by the appended claims.

What is claimed is:

1. A balloon catheter, comprising a catheter body, a balloon, a temperature-sensing element and a restricting member, the balloon disposed at a distal end of the catheter body, the temperature-sensing element comprising a wire and a temperature-sensing module, the temperature-sensing module disposed on the balloon or the catheter body, part of the wire of the temperature-sensing element arranged in a cavity of the catheter body so as to extend in an axial direction of the cavity of the catheter body, the restricting member disposed within the cavity of the catheter body and configured to positionally restrict the wire of the temperature-sensing element within the cavity of the catheter body, wherein the catheter body comprises an outer tube and a core rod disposed in the outer tube, the core rod protruding at a distal end thereof out of the outer tube, the outer tube and the core rod defining an annular cavity therebetween, wherein the balloon is connected at a distal end thereof to the core rod and at a proximal end thereof to the outer tube; the cavity of the catheter body comprises the annular cavity; and the restricting member is disposed in the annular cavity.

2. The balloon catheter of claim 1, comprising a plurality of temperature-sensing elements, wherein the restricting members are as many as the temperature-sensing elements, wherein the restricting members are spaced apart from one another within the cavity of the catheter body, and the wires of the temperature-sensing elements are passed through the restricting members respectively, or wherein at least one restricting member is comprised, which is less than the temperature-sensing elements, wherein some of the wires of the temperature-sensing elements pass through the restricting members, and each of the restricting member is configured for passage therethrough by the wire of one of the temperature-sensing elements.

3. The balloon catheter of claim 2, wherein non-adjacent ones of the wires of the temperature-sensing elements are equipped with the restricting members, or at least adjacent ones of the restricting members are staggered in the axial direction of the cavity of the catheter body.

4. The balloon catheter of claim 1, wherein the restricting member is fixedly connected to an inner wall surface of the outer tube or an outer wall surface of the core rod, or wherein the balloon catheter further comprises a control handle disposed at a proximal end of the catheter body, wherein the restricting member is fixedly connected to the control handle.

5. The balloon catheter of claim 1, comprising a plurality of restricting members, which are circumferentially spaced apart around an axis of the core rod and connected in series to form a ring-shaped structure.

6. The balloon catheter of claim 5, wherein the restricting members comprise sleeves configured for allowing the wire of the temperature-sensing element to pass through so as to positionally restrict the wire of the temperature-sensing element, wherein the sleeves are connected in series to form the ring-shaped structure, or wherein the restricting members comprise annular rings configured for allowing the wire of the temperature-sensing element to pass through so as to positionally restrict the wire of the temperature-sensing element, wherein the annular rings are connected in series to form the ring-shaped structure, and each adjacent two of the annular rings are connected by one linear-shaped elastomer.

7. The balloon catheter of claim 5, wherein the restricting members comprise a plurality of first restricting members and a plurality of second restricting members, the first restricting members configured to positionally restrict the wire of the temperature-sensing element, the second restricting members configured to positionally restrict the first restricting members, the first restricting members circumferentially spaced apart around the axis of the core rod, wherein the second restricting members are less than the first restricting members, wherein some of the first restricting members are provided thereover with the second restricting members, and the second restricting members are connected in series to form the ring-shaped structure; or wherein the second restricting members are as many as the first restricting members, wherein each of the first restricting members is provided thereover with a respective one of the second restricting members, and the second restricting members are connected in series to form the ring-shaped structure.

8. The balloon catheter of claim 7, wherein the first restricting members are sleeves and the second restricting members are annular rings, wherein the sleeves are disposed within the annular rings and configured for allowing the wire of the temperature-sensing element to pass through; the annular rings are connected in series to form the ring-shaped structure; and each adjacent two of the annular rings are connected by one linear-shaped elastomer.

9. The balloon catheter of claim 5, wherein one ring-shaped structure is formed or a plurality of ring-shaped structures spaced apart along the axial direction of the cavity of the catheter body are formed.

10. The balloon catheter of claim 9, comprising a plurality of temperature-sensing elements, wherein part of the wire of each of the temperature-sensing elements is arranged in the cavity of the catheter body so as to extend in the axial direction of the cavity of the catheter body; each of the restricting members that form the ring-shaped structure is inserted therein with the wire of one of the temperature-sensing elements; and the restricting members that form the ring-shaped structure are less than or as many as the temperature-sensing elements.

11. The balloon catheter of claim 1, wherein the restricting member comprises a sleeve configured for movable insertion and thus positional restriction therein of the wire of the temperature-sensing element, the sleeve comprising a narrower portion and at least one broader portion, the narrower portion having a luminal cross-sectional area smaller than a luminal cross-sectional area of the broader portion, wherein the wire of the temperature-sensing element comprises an extension and at least one curved portion, the curved portion configured to be able to be elongated or compressed, the extension disposed in the narrower portion, the curved portion disposed in the broader portion.

12. The balloon catheter of claim 11, comprising a plurality of temperature-sensing elements, part of the wire of each of the temperature-sensing elements arranged in the cavity of the catheter body so as to extend in the axial direction of the cavity of the catheter body, wherein the sleeves as many as the temperature-sensing elements are comprised, wherein the sleeves are spaced apart within the cavity of the catheter body; the wires of the temperature-sensing elements movably pass through the sleeves respectively; and the broader portions of the sleeves over the wires of at least adjacent ones of the temperature-sensing elements are staggered in the axial direction of the cavity of the catheter body, or wherein at least one sleeve is comprised, which is less than the temperature-sensing elements, wherein some of the wires of the temperature-sensing elements movably pass through the sleeves; each of the sleeves is configured for passage therethrough of the wire of one of the temperature-sensing elements; and the wires of the temperature-sensing elements that are equipped with the sleeves are non-adjacent ones, or the broader portions of the sleeves over the wires of at least adjacent ones of the temperature-sensing elements are staggered in the axial direction of the cavity of the catheter body.

13. The balloon catheter of claim 1, wherein the balloon is a double-layered balloon, wherein a plurality of temperature-sensing elements are comprised, the temperature-sensing modules of the plurality of temperature-sensing elements are arranged in an interlayer space of the double-layered balloon and/or on a portion of the catheter body located within the double-layered balloon.

14. An ablation system, comprising the balloon catheter of claim 1, an ablation energy output device and a control device, the ablation energy output device in communication with the balloon catheter, the ablation energy output device configured to provide ablation medium to the balloon catheter, the control device configured to control, based on temperature information detected by the temperature-sensing element(s), the ablation energy output device to adjust a temperature of the ablation medium so as to maintain a surface temperature of the balloon within a predefined ablation temperature range.

* * * * *